United States Patent
Sorita et al.

(10) Patent No.: US 6,175,111 B1
(45) Date of Patent: Jan. 16, 2001

(54) METHOD FOR DIAGNOSIS OF COMPONENTS INSIDE TURBINE GENERATOR

(75) Inventors: Tetsuji Sorita; Shintaro Minami; Hiroshi Adachi, all of Tokyo; Mitsuru Takashima; Masayuki Misawa, both of Osaka, all of (JP)

(73) Assignees: Mitsubishi Denki Kabushiki Kaisha, Tokyo; The Kansai Electric Power Co., Inc., Osaka, both of (JP)

( * ) Notice: Under 35 U.S.C. 154(b), the term of this patent shall be extended for 0 days.

(21) Appl. No.: 09/124,967

(22) Filed: Jul. 30, 1998

(30) Foreign Application Priority Data

Sep. 30, 1997 (JP) .................................................. 9-265815

(51) Int. Cl.[7] ...................................................... H01J 49/00
(52) U.S. Cl. ........................ 250/282; 73/23.36; 73/23.37
(58) Field of Search .................................. 250/282, 281, 250/288; 73/23.22, 23.31, 23.35, 23.36, 23.37

(56) References Cited

U.S. PATENT DOCUMENTS 5,465,607  *  11/1995  Corrigan et al. ...................... 250/282

OTHER PUBLICATIONS

Kelly et al., "Early Detection and Diagnosis of Overheating Problems in Turbine Generators by Instrumental Chemical Analysis", IEEE Transactions on Power Apparatus and Systems, vol. PAS–95, No. 3, May/Jun. 1976, pp. 879–886.

"Generator Condition Monitor", Mitsubishi Electronics Technical Journal, vol. 54., No. 7, 1980, pp. 1 (479)–5 (483).

Carson et al., "Immediate Detection of Overheating in Gas–Cooled Electrical Machines", IEEE Winter Power Mtg., New York, New York, Jan. 31–Feb. 5, 1971, pp. 1–9, Paper No. CP 154–PWR.

* cited by examiner

Primary Examiner—Kiet T. Nguyen
(74) Attorney, Agent, or Firm—Leydig, Voit & Mayer, Ltd.

(57) ABSTRACT

A method for diagnosis of components inside a turbine generator includes collecting and measuring organic substances present in a gas inside the turbine generator to obtain data (first data). Before the collecting, organic substances generated from each component inside the turbine generator due to heat, discharge, corrosion, or friction, are measured to compile data (second data). The first data is compared to the second data to determine whether the first data includes the same data as in the second data to detect deterioration of the components inside the turbine generator.

7 Claims, 5 Drawing Sheets

METHOD FOR DIAGNOSIS OF COMPONENTS INSIDE TURBINE GENERATOR

BACKGROUND OF THE INVENTION

1. Field of the Invention

This invention relates to a method for diagnosis of components used inside a turbine generator for power supply, by which method the state of a gas inside the turbine generator is investigated to diagnose the components.

2. Description of the Prior Art

Roughly two methods have been known to diagnose components used inside a turbine generator by investigating a gas inside the turbine generator.

One of the methods is adopted in a device called "Generator-ConditionMonitor," a product of Environment-One, the United States, as shown, for example, in publication 1 (IEEE Conference Paper, 71C, p. 154 (1971)). This device is already commercially available.

The Generator-Condition-Monitor and the Ion-Chamber-Detector in common use are the same in the principle of action and the way of diagnosis.

Figure 6:
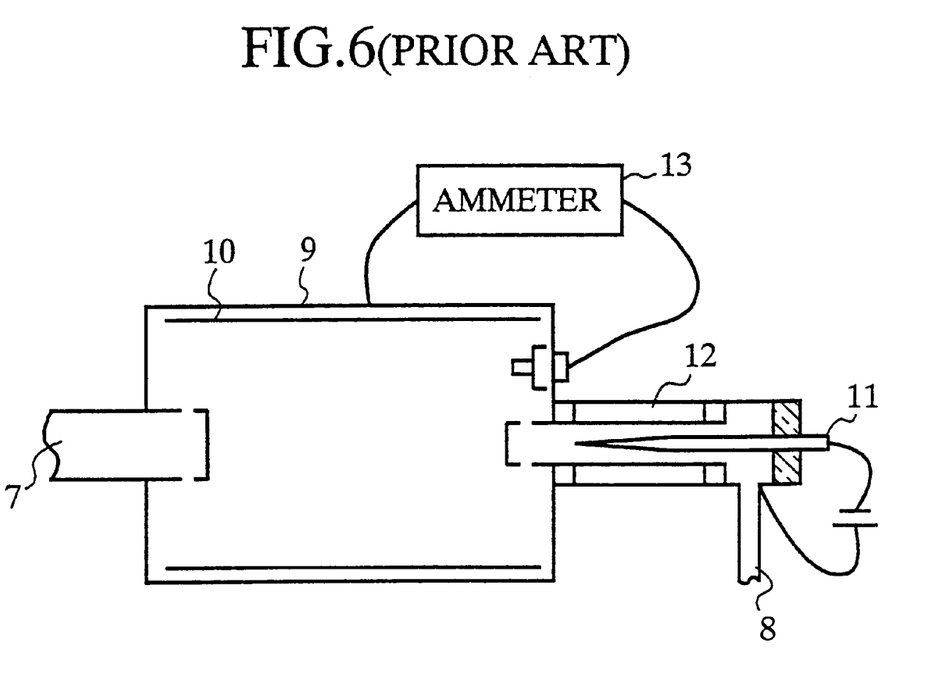
FIG. 6 is a structural view of an Ion-Chamber-Detector in general use.

FIG. 6 is a structural diagram of the Ion-Chamber-Detector in general use. This Ion-Chamber-Detector will be described first.

In FIG. 6, the reference numeral 7 designates a power instrument line for introduction of a gas that has filled up a turbine generator. In the publication 1, a hydrogen gas is used as this gas. The reference numeral 9 designates a device container, and the reference numeral 10 designates an a radiation source for irradiating the gas, which has been introduced into the device container 9, with α rays. The reference numerals 11 and 12 designate, respectively, an electrode for applying a voltage, and an electrode for applying a voltage of a polarity opposite to the polarity of the electrode 11. The reference numeral 13 designates an ammeter for measuring an electric current flowing between the electrode 12 and the device container 9 at zero potential. The reference numeral 8 designates an outlet for the gas.

The action of the device illustrated in FIG. 6 will be described next.

Part of the hydrogen gas filled in the turbine generator is guided to the power instrument line 7, and then introduced into the device container 9 through the opening of the power instrument line 7. The hydrogen gas introduced into the device container 9 is ionized with a rays irradiated by the a radiation source 10. Then, the gas is guided by an electric field formed between the electrode 11 and the electrode 12, and flowed into the turbine generator again past the gas outlet 8.

If the hydrogen gas inside the turbine generator is free from organic substances, the ionized hydrogen molecules are light and easily movable. Thus, these molecules move easily under the electric field between the electrodes 11 and 12, reaching the electrode 12. As a result, a certain electric current is detected by the ammeter 13. If the hydrogen gas inside the turbine generator contains organic substances, on the other hand, the ionized organic substances are heavy and minimally move. This results in a decreased proportion of the hydrogen gas reaching the electrode 12. Consequently, a smaller electric current than with the hydrogen gas containing no organic substances is detected by the ammeter 13.

In other words, when the gas in the turbine generator is free from organic substances, a relatively large current flows through the ammeter 13. Whereas when the gas in the turbine generator contains organic substances, only a small current flows through the ammeter 13. Furthermore, the decrease in the current differs according to the amount of the organic substances entering the device container 9. The larger the amount of the organic substances, the greater the decrease in the current becomes, so that the value of the current becomes closer to zero amperes.

A conventional method of diagnosis using the Ion-Chamber-Detector shown in FIG. 6 will be described.

When the turbine generator is assumed to be working normally, the value of an electric current is detected by the ammeter 13. This value is recorded as the level of current during normal operation. Constantly or where necessary, the gas is introduced through the gas introduction line 7 into the device container 9 to detect an electric current. If the value of this current is lower than the previously recorded normal level, the total amount of the organic substances in the gas inside the turbine generator is presumed to have increased from the level during normal operation. This increase in the amount of the organic substances in the gas means that components composed of organic materials inside the turbine generator may be thermally decomposing. Thus, monitoring of a decrease in the current detected, namely, the total amount of the organic substances in the gas, makes it possible to diagnose whether the components inside the turbine generator are overheating or not.

In short, one of the conventional diagnostic methods has been to monitor the total amount of the organic substances in the gas inside the turbine generator, and estimate whether or not overheating is occurring in the components composed of organic materials and used in the turbine generator.

The second conventional method is described in publication 2 (IEEE Trans., PAS-100, p. 4983 (1981)) and publication 3 (IEEE Trans., PAS-95, p. 879 (1976)). This method comprises passing a gas in a turbine generator through a filter or an adsorbent, and then analyzing organic substances trapped in the filter or adsorbent by gas chromatography to identify the organic substances in the gas inside the turbine generator.

In the publication 2, moreover, a substance which will be released upon overheating of a component inside a turbine generator is incorporated into the component beforehand. Then, the substance in the gas detected by gas chromatography in the above manner is checked to see if it is identical with the incorporated substance. It is diagnosed thereby whether the component inside the turbine generator is overheating or not.

The publication 3 describes that the gas chromatographic identification of the organic substances in the turbine generator can result in a diagnosis of whether overheating is occurring or not. However, it does not describe a concrete method for diagnosis, nor the relation between overheating and the organic substances.

In summary, one of the conventional methods for diagnosis is to monitor the total amount of organic substances in the gas inside the turbine generator, thereby estimating the presence or absence of overheating in the organic materials used inside the turbine generator. The other method is to collect organic substances in the gas inside the turbine generator and identify them by means of a gas chromatograph, thereby estimating the presence or absence of overheating in the organic materials in the components used inside the turbine generator.

One of the above earlier methods for diagnosis of components inside the turbine generator detects the total amount of organic substances in the gas inside the turbine generator.

Thus, it cannot discriminate among numerous organic substances present in the gas. There may be a case in which an organic substance unrelated to the materials for the components, such as a lubricating oil, is present in the gas, and no abnormality occurs in the turbine generator. That method sometimes diagnosed this case as a case of overheating. Even when diagnosing overheating correctly, the method was unable to specify which component was suffering overheating.

According to the other diagnostic method, it is possible to distinguish among organic substances in the gas inside the turbine generator by gas chromatography. However, information is lacking about which substance is suitable for use as a standard of judgment for diagnosis of the material, or what concrete procedure or method is suitable for diagnosis. This has posed extreme difficulty in making a precise diagnosis.

Besides, the above conventional method of diagnosis incorporates, beforehand, a substance, which can be easily released upon heating, into the component inside the turbine generator, thereby permitting a diagnosis of whether overheating is occurring or not, and the identification of the overheated component. With this method, however, it has been essential to incorporate, in advance, a special material into the component when producing the turbine generator. This has required more than ordinary labor and cost for the production of the component. This method has been directed only at a turbine generator containing a special substance in the components. With a previously produced turbine generator containing no special substance in the components, no effects were obtained at all. Actually, most of the turbine generators previously manufactured are free from such a special substance. Hence, this method for diagnosis is effective in an extremely limited number of the turbine generators now in operation.

Furthermore, all the above-described diagnostic methods that have been used in the diagnosis of turbine generators have merely detected whether overheating of the components is present or absent. They have been unable to diagnose heat deterioration at nearly the operating temperature of the generator that does not lead to overheating, or deterioration due to discharge, corrosion or friction.

SUMMARY OF THE INVENTION

Under these circumstances, it is a primary object of the present invention to obtain a method for diagnosis of components inside a turbine generator, which method can detect the heat-, discharge-, corrosion- or friction-associated deterioration of the component inside the turbine generator without incorporating a special substance into the component inside the turbine generator, and which method can also predict the life of the deteriorated component from its degree of deterioration.

It is a secondary object of the present invention to obtain a method for diagnosis of components inside a turbine generator, which method can pinpoint the location of deterioration by identifying the deteriorated component, can determine the cause of deterioration, and enables rapid and appropriate action to be taken.

To attain the above objects, according to a first aspect of this invention, there is provided a method for diagnosis of components inside a turbine generator, which comprises the steps of collecting organic substances present in a gas inside the turbine generator; measuring the collected organic substances to obtain first data on the organic substances; measuring, beforehand, organic substances generated from each component inside the turbine generator owing to heat, discharge, corrosion or friction, to compile second data on the organic substances; and checking the first data and the second data against each other to judge whether the same data as in the second data is present or absent in the first data. According to this method, there is obtained the effect of detecting the heat-, discharge-, corrosion- or friction-induced deterioration of the component inside the turbine generator, without incorporating, beforehand, a special substance into the component inside the turbine generator.

According to a second aspect of the invention, there is provided the method for diagnosis of components inside a turbine generator, further including the step of detecting changes over time in the same data as in the second data, the same data being present in the first data. This method gives the effect of predicting the life of the component.

According to a third aspect of the invention, there is provided the method for diagnosis of components inside a turbine generator, further including the step of identifying a component undergoing deterioration, or determining the cause of deterioration of the component, on the basis of the same data as in the second data, the same data being present in the first data. This method gives the effect that rapid and appropriate action, such as elimination of the cause of deterioration, can be taken.

According to a fourth aspect of the invention, there is provided the method for diagnosis of components inside a turbine generator, wherein data obtained by gas chromatography, infrared absorption spectroscopy, reflection infrared spectroscopy, mass spectrometry, or X-ray photoelectron spectroscopy are used as the first data and the second data. This method gives the effect of facilitating the diagnosis of deterioration.

According to a fifth aspect of the invention, there is provided the method for diagnosis of components inside a turbine generator, wherein the checking of the first data and the second data against each other is performed by a computer. This method gives the effect that the diagnosis of deterioration can be made in a short time.

According to a sixth aspect of the invention, there is provided the method for diagnosis of components inside a turbine generator, wherein only data on aromatic hydrocarbons with a molecular weight of 92 or more among the first data and the second data are used as a standard of judgment at the time of the data checking. This method produces the effect that the procedure for diagnosis of the turbine generator can be markedly simplified, whereby the duration of diagnosis can be shortened.

According to a seventh aspect of the invention, there is provided the method for diagnosis of components inside a turbine generator, wherein the gas withdrawn from the turbine generator is passed through an adsorbent to collect the organic substances present in the gas inside the turbine generator. This method gives the effect that the organic substances inside the turbine generator are concentrated to facilitate their analysis, and a flammable hydrogen gas, etc. need not be carried to an analyzer, so that operation can be performed safely.

BRIEF DESCRIPTION OF THE DRAWINGS

Other objects and advantages of the present invention will become understandable more clearly by reading the following detailed description with reference to the accompanying drawings, in which.

DETAILED DESCRIPTION OF THE PREFERRED EMBODIMENTS

The preferred embodiments of the present invention will now be described in detail by reference to the appended drawings.

Figure 1:
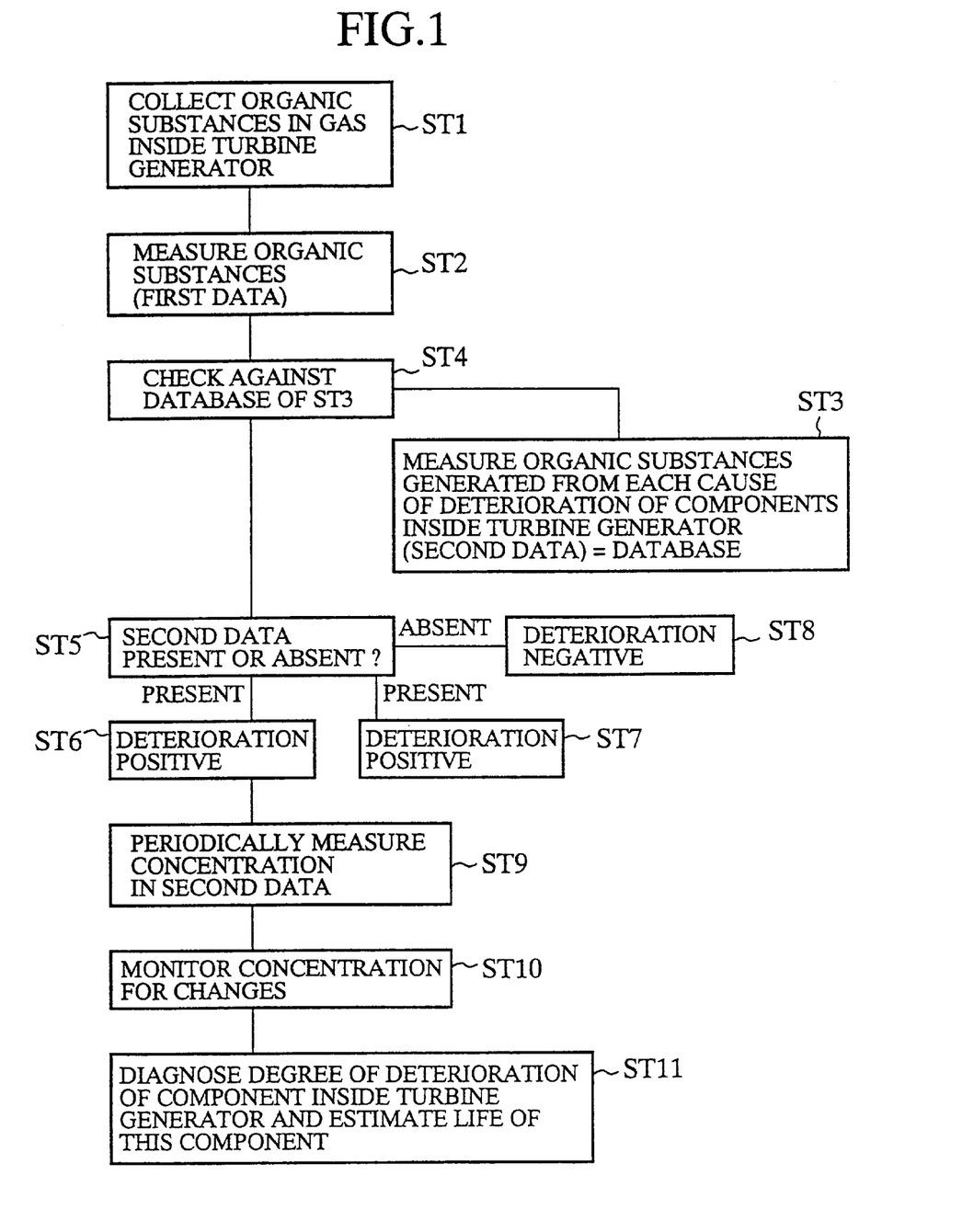
FIG. 1 is a flow chart showing a procedure for diagnosis in the method for diagnosis of components inside a turbine generator in accordance with the present invention.

FIG. 1 is a flow chart showing a procedure for diagnosis in the method for diagnosis of components inside a turbine generator in accordance with the present invention.

Organic substances present in a gas inside the turbine generator are collected (step ST1), and measurements obtained by a suitable measuring instrument are used as the first data (step ST2).

Separately, organic substances generated from the same materials as, or similar materials to, the materials constituting components inside the turbine generator owing to deterioration by heat, discharge, corrosion or friction are measured, and the measurements obtained are used as the second data. The second data obtained on the respective components inside the turbine generator are grouped together into a database beforehand (step ST3).

Then, the first data is checked against the second data (step ST4). If data included in the grouped second data is present in the first data, this is indicative of deterioration due to heat, discharge, corrosion or friction occurring in any of the components inside the turbine generator (Steps ST5, ST6 and ST7). If data included in the group of the second data is absent in the first data, it is judged that no deterioration takes place in the components inside the turbine generator (step ST8).

If the presence or absence of deterioration is judged only once, a judging action ends with the above procedure (steps ST7 and ST8).

When the progress status of deterioration is judged over time, however, the concentration of the organic substance in the first data that exists in the grouped second data is measured periodically (step ST9) to monitor the concentration of this organic substance for changes (step ST10). The concentration varying (increasing) with time leads to a judgment that deterioration is proceeding (step ST11).

In this manner, the concentration of the organic substance in the group of the second data that is present in the first data is periodically measured for monitoring of changes. This monitoring enables the life of the component inside the turbine generator to be predicted based on its degree of deterioration.

In the flow chart of FIG. 1 showing the means of diagnosis, the organic substance existent in the gas inside the turbine generator is not identified, but checked against the database storing the second data. If the organic substance checked is identified as in the embodiment to follow, the progress status of deterioration can be diagnosed accurately.

Needless to say, the above method for diagnosis obviates the need to incorporate a special substance into the component inside the turbine generator.

This method for diagnosis of the components inside the turbine generator according to the present invention has been described in connection with the diagnosis of various types of deterioration. However, deterioration due to other causes, such as overheating, can be diagnosed similar to the diagnosis of the above types of deterioration, if a database on deterioration of the components from such other causes including overheating is rendered ready for use.

Figure 2:
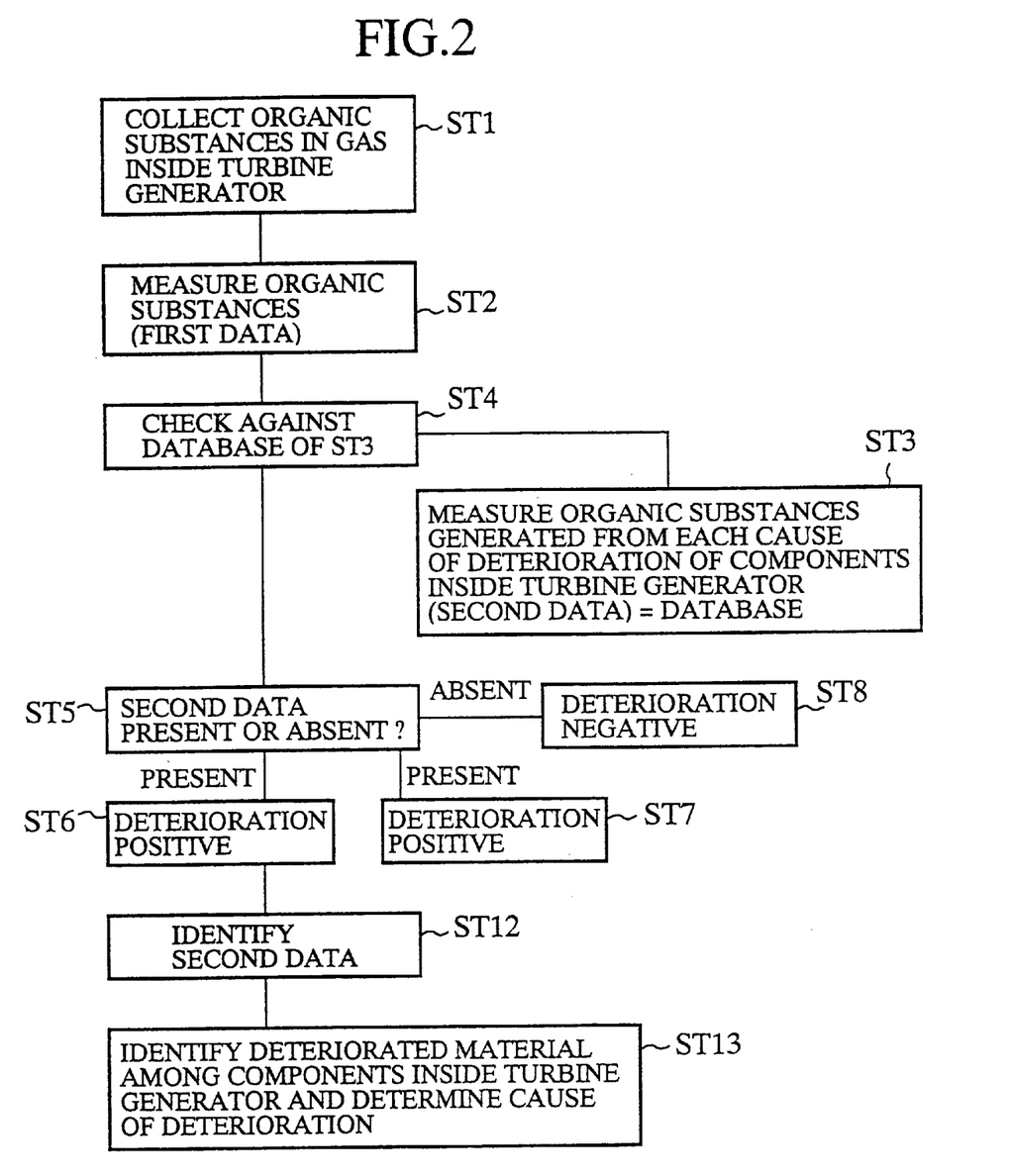
FIG. 2 is a flow chart showing another procedure for diagnosis in the method for diagnosis of components inside a turbine generator in accordance with the present invention.

FIG. 2 is a flow chart showing another procedure for diagnosis in the method for diagnosis of components inside a turbine generator in accordance with the present invention. In FIG. 2, the same steps as in the flow chart of FIG. 1 are assigned the same step numbers, and their detailed explanations will be omitted.

According to this diagnostic method, the first data and the group of the second data (database) are obtained in the same way as in the diagnostic method illustrated in FIG. 1 (steps ST1 to ST3). Then, the first data and the second data group are checked against each other (step ST4). If data included in the second data group is present in the first data, it is judged that deterioration due to heat, discharge, corrosion or friction is occurring in the components inside the turbine generator (Steps ST5, ST6 and ST7). If data included in the second data group is absent in the first data, on the other hand, it is judged that no deterioration is taking place in the components inside the turbine generator (step ST8).

In this method, when the checking of the first data and data in the second data group has shown deterioration of the components, measurement is continued (step ST6). In this case, it is identified which cause of deterioration of which component generated the organic substance corresponding to the data in the second data group against which the first data is checked (step ST12). This identification gives the knowledge of what sort of deterioration is being exerted on which component inside the turbine generator due to what cause (step ST13). From this knowledge, the operator can quickly and appropriately taken action, such as elimination of the cause.

That is, even if data in the second data group exists in the first data, this data may be based on a cause unrelated to the deterioration of the component, for example, a lubricating oil. In this case, this data can be neglected, and diagnosis can be made without influence from such a cause.

According to the above method for diagnosis, there is no need, of course, to incorporate a special substance into the component inside the turbine generator.

This method for diagnosis of the components inside the turbine generator according to the present invention has been described in connection with the diagnosis of the above-mentioned various causes of deterioration and the deteriorated materials. However, deterioration due to other causes, such as overheating, can be diagnosed similar to the diagnosis of the above types of deterioration, if a database on deterioration of the components from such other causes including overheating is made ready for use.

According to the method for diagnosis of components inside the turbine generator, if the first data and the second data are data from gas chromatography, infrared absorption spectroscopy, reflection infrared spectroscopy, mass spectrometry, or X-ray photoelectron spectroscopy, the first data and the second data can be obtained easily.

According to the method for diagnosis of components inside the turbine generator, moreover, diagnosis can be made in a short period of time, by taking the first data and the second data into a computer, and checking them against each other on the computer.

According to the method for diagnosis of components inside the turbine generator, furthermore, aromatic hydrocarbons with a molecular weight of 92 or more are used as a standard of judgment for diagnosis, instead of using aliphatic hydrocarbons as a standard of judgment for diagnosis. By so doing, the procedure for diagnosis of the turbine generator, in particular, can be markedly simplified, whereby the duration of diagnosis can be shortened.

Besides, the gas is withdrawn from the turbine generator, and only organic substances present in the gas are accumulated in an adsorbent. As a result, the organic substances inside the turbine generator are concentrated, and thus their analysis becomes easy. Also, a flammable hydrogen gas, etc. need not be carried to an analyzer, so that operation can be performed safely.

Embodiment 1

Figure 3:
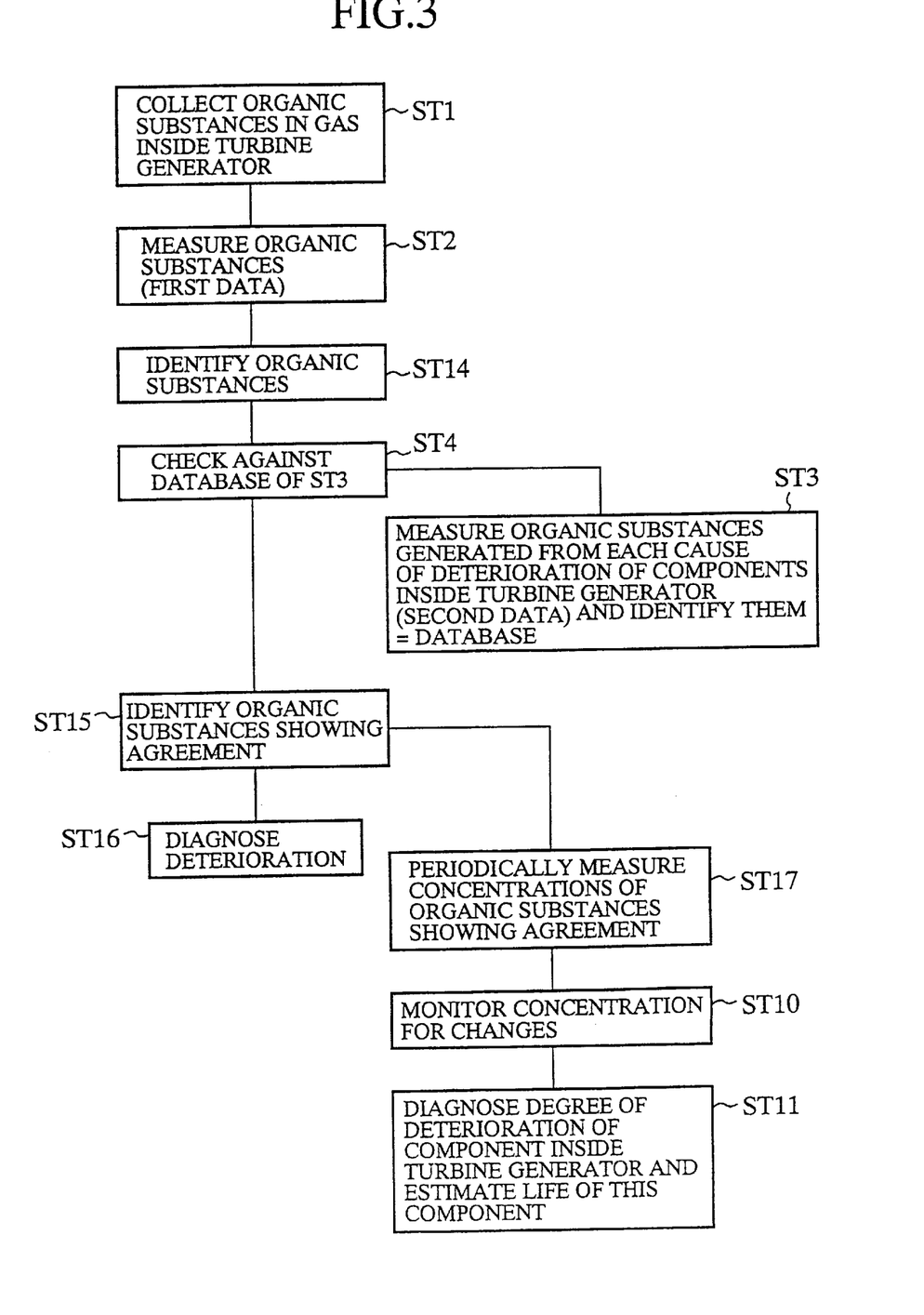
FIG. 3 is a flow chart showing a procedure for diagnosis related to the method for diagnosis of components inside a turbine generator as a first embodiment of the present invention.

FIG. 3 is a flow chart showing a procedure for diagnosis related to the method for diagnosis of components inside a turbine generator as a first embodiment of the present invention. In this drawing, the same steps as the steps of the flow charts shown in FIGS. 1 and 2 are assigned the same step Nos. The method for diagnosis of Embodiment 1 will now be described in detail.

Figure 4:
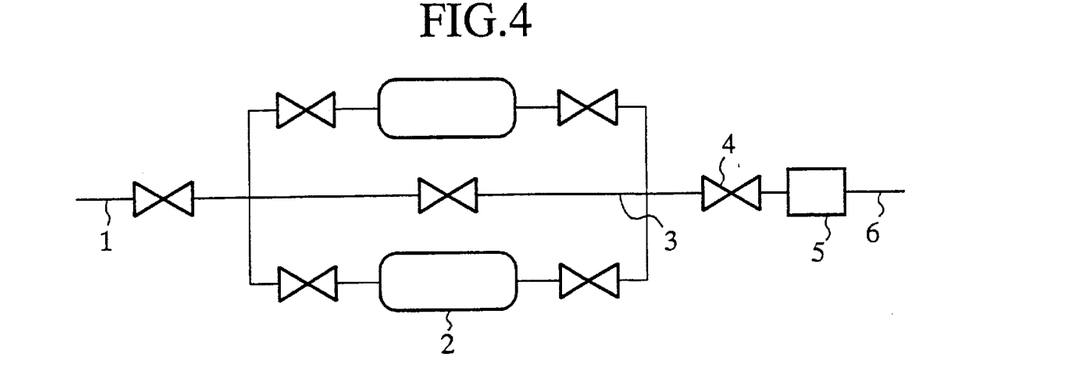
FIG. 4 is an explanation drawing showing the configuration of a collector of a gas inside a turbine generator related to the method for diagnosis of components inside a turbine generator in accordance with the present invention.

FIG. 4 is an explanation drawing showing the configuration of a gas collector for a turbine generator employed in this Embodiment 1. In FIG. 4, the reference numeral 1 designates a gas inlet line for guiding the gas inside the turbine generator. The reference numeral 2 designates an organic substance adsorption pipe packed with an adsorbent. The reference numeral 3 designates a bypass line. The reference numeral 4 designates a valve. The reference numeral 5 designates a flow rate controller for regulating the flow rate of the gas introduced into the gas collector, and reading the flow rate and the accumulated flow rate. The reference numeral 6 designates an outlet for the gas. The organic substance adsorption pipe 2 may be a steel cylinder for storing a gas.

Instead of using the gas collector shown in FIG. 4, the gas inside the turbine generator may be directly introduced into an analyzer such as a gas chromatograph or an infrared absorption spectroscope.

At step ST1 in this first embodiment, any special substance need not be incorporated into the materials inside the turbine generator. If the gas inside the turbine generator is used as such, this gas may be introduced into the gas collector shown in FIG. 4 to trap organic substances in the gas.

For example, the gas collector shown in FIG. 4 was connected to a line of a hydrogen-cooled turbine generator with a generated power of 600 MW which was in operation. A hydrogen gas inside the turbine generator was introduced into the gas inlet 1, and valves on both sides of one of the organic substance adsorption pipes 2 were opened to pass the hydrogen gas up to the gas outlet 6. The organic substance adsorption pipe 2 was metallic, and packed with 2.5 g of an absorbent (registered trademark: TENAX, Enka Research Institute). The gas discharged through the gas outlet 6 was released to the atmosphere. The amount of the hydrogen gas passed was set at 2 liters/min by the flow rate controller 5, and the hydrogen gas was passed through the organic: substance adsorption pipe 2 for 25 minutes, whereafter all the valves were closed. In this fashion, organic substances in 50 liters of hydrogen gas were trapped in one of the organic substance adsorption pipes 2. If desired, the gas inside the turbine generator may be passed through the other organic substance adsorption pipe 2 to increase the number of the samples for analysis. However, one sample per day was used in this embodiment.

After trapping of organic substances contained in the hydrogen gas was completed, the organic substance adsorption pipe 2 as the sample was detached. Then, for the measurement of organic substances at step ST2, the organic substance adsorption pipe 2 was heated to 250° C. by a heat desorbing device or head space sampler attached to a gas chromatograph. The organic substances adsorbed to the inside of the pipe were introduced into the gas chromatograph equipped with a mass spectrometer.

The organic substances introduced into the gas chromatograph were analyzed by programmed temperature gas chromatography using a nonpolar column. This programmed temperature method was performed under the following conditions: an initial column temperature of 40° C., a programming rate of 5° C./min, and a final temperature of 260° C. A detector used was a quadrupole mass spectrometer, and detection was performed with a scanned mass number in the range of 35 to 500.

A plurality of organic substances present in the gas inside the turbine generator can be detected by this method. Based on the mass spectra of the thus detected organic substances (first data), the respective organic substances can be identified or estimated (step ST14). Toluene, dimethylbenzene, decane, trimethyidecane, and phenol derivatives such as dimethylethylphenol and methyi carbamate were identified as the organic substances inside the turbine generator.

Simultaneously with the identification of the organic substances, the mass of each organic substance was measured from the gas chromatographic data, and the concentration of each organic substance in the turbine generator gas was calculated.

Separately, organic substances generated from the same materials as for the components inside the turbine generator, for example, a cured epoxy resin, under the action of heat or discharge were measured, and identified for use as the second data. A database on the substances produced from the cured epoxy resin was constructed from a group of the second data (step ST3).

It turned out that phenol derivatives, i.e., dimethylethylphenol and methyl carbamate, were present in the substances produced from the cured epoxy resin (second data).

The above database may be prepared from the results of internal experiments, or from known data.

Of the procedure for diagnosis illustrated in FIG. 3, the steps to be implemented after step ST13, the organic substance identification step, will be described.

The data from gas chromatography and mass spectrometry of the organic substances in the turbine generator (i.e., the first data) were taken into a computer, and checked against the previously prepared second data (e.g., substances generated from the cured epoxy resin) on the computer (step ST4). This checking showed the phenol derivatives of the second data to be present in the first data on the organic substances inside the turbine generator (step ST15). Thus, a diagnosis was made of heat- or discharge-associated deterioration occurring in the cured epoxy resin portion inside the turbine generator (step ST16).

Inside the turbine generator, many kinds of organic substances were present, as have been stated, besides the phenol derivatives. Thus, there is no need to examine the concentrations in the gas of organic substances restricted to those resulting from the cured epoxy resin. In the foregoing case, the concentrations of such other organic substances in the gas may be examined in addition to the phenol derivatives.

In the instant embodiment, the organic substances included in the first data and the second data have been identified. However, deterioration can be diagnosed simply by knowing whether data in the second data group exists in the first data or not. Even if the organic substances are not identified, it is enough that measurements increasing with time or a group of spectral measurements be present in the gas. Feedback of these parameters to the database to make it of practical use.

Instead of using the whole of the second data from the respective components as a standard of judgment, it is permissible to find out a characteristic point in the second data group, and utilize it as an indicator. This will facilitate diagnosis.

However, we, the inventors, have found that aliphatic hydrocarbons and aromatic hydrocarbons with a molecular weight of less than 92 are totally unrelated to the deterioration or abnormality of the materials. Thus, they are not utilized as standards of judgment when doing the check.

The phenol derivatives detected in this embodiment were all aromatic hydrocarbons with a molecular weight of 92 or more.

It is desirable to construct a database on organic substances which occur when as many components inside the turbine generator as possible deteriorate for various causes. However, it is effective to construct a database on particularly important materials as in the instant embodiment.

Then, the first part of the flow chart of FIG. 3, i.e., the collection (step ST1) and identification (step ST14) of organic substances in the gas, was repeated at intervals of one month (step ST17) to detect the time course of the concentrations of phenol derivatives in the turbine generator gas, such as dimethylethylphenol and methyl carbamate. This interval period is not restricted, but should desirably be shortened if fluctuations in the concentrations grow large.

Diagnosis of the components inside the turbine generator was made based on the amounts of changes over time in the concentrations of the phenol derivatives, dimethylethylphenol and methyl carbamate (step ST10). The concentration of methyl carbamate kept a constant value of 0.2 ppb from the initial measurement until after a lapse of one year. The concentration of dimethylethylphenol, on the other hand, was 0.8 at the initial measurement, which became 0.9, 1.0, 1.1, 1.2 ppb and so on in this sequence, showing a tendency toward increasing by 0.1 ppb at intervals of 1 month.

In the light of the above findings, the period of time elapsing until the dimethylethylphenol concentration reached 10.0 ppb was regarded as the life of the cured epoxy resin inside the turbine generator. If this concentration is assumed to increase at this rate, it will come to 10.0 ppb after 92 months. Thus, the life of the cured epoxy resin inside the turbine generator could be estimated at about 92 months, namely, 7 years and 8 months (step ST11).

This full length of the estimated life showed that there would be no need now to renew the material in question, and it would suffice to begin a diagnosis again about 5 years from now and proceed with preparations for the renewal of the material.

According to the instant embodiment, the period of time until the arrival of the concentration at 10.0 ppb has been designated as the life of the material. This is because when the concentration is about 10.0 ppb, the amount of the material decomposed is about 5%, which may make the material subject to dielectric breakdown. The concentration that determines the life may be set at, say, 5.0 ppb for increased safety, or a high concentration of 50.0 ppb or even 1,000 ppb may be set depending on the material. Alternatively, the way of determining the concentration for estimation of life may be by setting a value which is so-and-so times the current concentration.

Anyway, if the estimated life is within 1 year, the material can be renewed promptly to prevent a possible accident. When the life has been diagnosed as 1 year or more, diagnosis is conducted periodically to reconfirm the life, and the stoppage of the turbine generator and the renewal of the material can be performed at proper time points.

The instant embodiment concerns sampling of the gas from the turbine generator during operation. However, the effects of the present invention are obtained while the turbine generator is at a standstill or during no-load operation.

Embodiment 2

Figure 5:
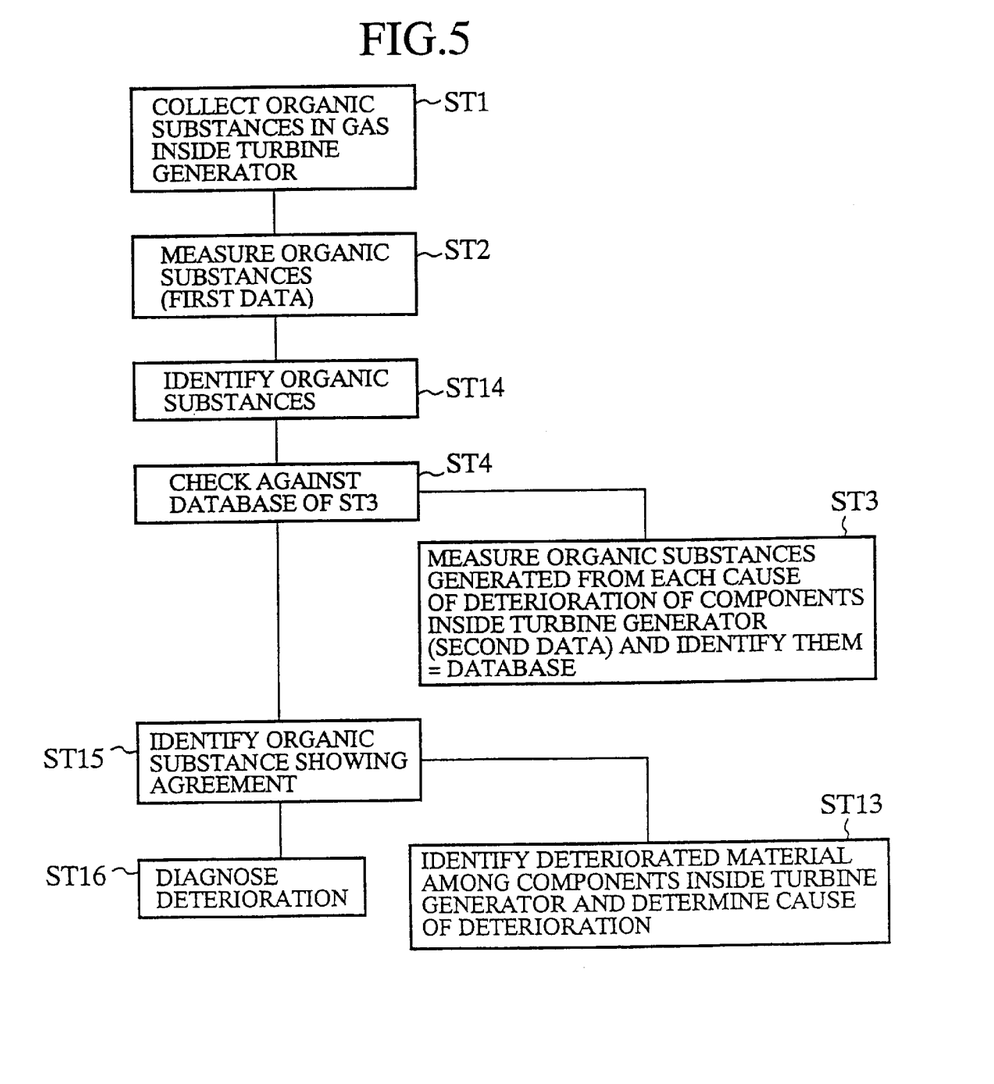
FIG. 5 is a flow chart showing a procedure for diagnosis related to the method for diagnosis of components inside a turbine generator as a second embodiment of the present invention.

FIG. 5 is a flow chart showing a procedure for diagnosis related to the method for diagnosis of components inside a turbine generator as a second embodiment of the present invention. In this drawing, the same steps as the steps of the flow charts of FIGS. 1 to 3 are assigned the same step numbers.

In the instant embodiment as well, organic substances in the gas inside the turbine generator were identified using the gas collector shown in FIG. 4. First, organic substances in the gas were trapped in the same way as in Embodiment 1 from a 250 MW turbine generator during operation (step ST1). The remaining gas after trapping of the organic substances was returned to the turbine generator.

Then, the sample was introduced via a heat desorbing device into a gas chromatograph and a mass spectrometer in the same manner as in Embodiment 1 to make an analysis (first data) (step ST2). In the instant embodiment, a minimally polar column was used, and the programming rate was set at 2° C./min. The analysis showed the presence of toluene, decane and methylphenol as organic substances in the gas inside the turbine generator (step ST14).

Separately, a plurality of components used in the turbine generator, i.e., a cured epoxy resin (type A cured epoxy resin) as an insulation-to-the-earth material for a stator coil, a cured epoxy resin (type B cured epoxy resin) as a material around the stator coil, and a cured phenolic resin as a stator adhesive, were targeted for measurement. Organic substances generated from the respective materials by heat or discharge were measured (second data), and identified to construct a database beforehand (step ST3).

The methods and procedures for identifying the organic substances generated by these materials may be any methods and procedures. In the instant embodiment, the three kinds of materials have been targeted, but more kinds of organic materials for components inside the turbine generator may be selected as targets.

Next, the methods of identifying the deteriorated material and determining the cause of deterioration will be described in accordance with the procedure shown in FIG. 5.

According the above database, methylphenol was recognized as a substance generated by heat from the cured epoxy resin (type B cured epoxy resin) as the material around the stator coil. However, methylphenol was not observed among the heat- or discharge-generated substances from the cured epoxy resin (type A cured epoxy resin) and cured phenolic resin, the materials other than the materials around the stator coil.

As stated earlier, methylphenol was found in the organic substances contained in the turbine generator gas. Thus, the occurrence of deterioration in the turbine generator was diagnosed (steps ST15, ST16). It was also diagnosed that deterioration or abnormality occurred in the cured epoxy resin (type B cured epoxy resin) portion around the stator coil inside the turbine generator, and that this deterioration was due to heat rather than discharge (step ST13).

As a result of the above diagnoses, the turbine generator was stopped before an accident would occur. Then, the material was renewed only at the site of abnormality expected from the diagnosis, whereafter operation was resumed in a short period. Since heat was estimated to be the cause of the abnormality, moreover, necessary action could be taken.

Embodiment 3

The method for diagnosis as a third embodiment of the present invention will be described. This embodiment is also practiced on the basis of the procedure illustrated in FIG. 3.

The object to be diagnosed was a hydrogen-cooled turbine generator with a power of 200 mW that was at a standstill. For the analysis of the gas inside the turbine generator, it is better to sample the gas out of the turbine generator during operation. This will lead to an accurate diagnosis, but it is possible to make a diagnosis even during halts of the turbine generator.

As a gas collector for the turbine generator, there was used the gas collector of FIG. 4 with the sample adsorption pipe 2 replaced by a steel cylinder for sample collection. 20 Liters of gas at 3 atmospheres inside the turbine generator was trapped in this sampling cylinder, and then valves on both sides of the cylinder were closed (step ST1).

The hydrogen gas from inside the turbine generator that was stored in the cylinder was transferred into a gas cell for an infrared absorption spectroscope with an optical path length of 20 meters. The gas cell was mounted in a Fourier transform infrared absorption spectroscope (FTIR) to measure the infrared absorption spectrum of the gas inside the turbine generator (first data) (step ST2). The measurement showed that an aromatic hydrocarbon having a hydroxyl group and an aliphatic hydrocarbon of an unknown structure were present inside the turbine generator (step ST14).

In identifying the organic substances in the gas inside the turbine generator, it is desirable to make the names of substances as clear as possible. As indicated in this embodiment, however, naming the types of substances enables diagnosis according to the present invention.

Separately, the same Fourier transform infrared absorption spectroscope as in the analysis of the gas inside the turbine generator was used to measure organic substances (second data) generated upon heating from the same type of cured polyester resin as the component inside the turbine generator. Based on the measurements, a database was organized beforehand (step ST3). In the second data, the presence of an aromatic hydrocarbon having a hydroxyl group was recognized, while no aliphatic hydrocarbon was noted.

Then, the first data and the second data were checked against each other (step ST4), with the result that the gas inside the turbine generator was also found to contain the same aromatic hydrocarbon with a hydroxy group as the organic substance generated from the cured polyester resin by heat (step S15). Hence, a diagnosis was made of heat deterioration taking place in the component inside the turbine generator (step ST16).

Next, changes over time in the concentration of the hydroxyl-containing aromatic hydrocarbon inside the turbine generator were investigated for diagnosis of the life.

As in the aforementioned procedure, the gas inside the turbine generator was trapped in the steel container at 3-month intervals, and analyzed with a Fourier transform infrared absorption spectroscope. From the absorption intensity of the aromatic hydrocarbon with a hydroxyl group, its concentration was measured (step ST17). The concentration measured at intervals of 3 months from the date of the initial gas trapping remained at a constant value of 10 ppb over the course of 2 years (step ST10).

This finding led to a diagnosis of little deterioration occurring in the component inside the turbine generator, the target for diagnosis according to the instant embodiment. Renewal of the material was found unnecessary for the time being (step ST11).

Embodiment 4

The method for diagnosis as a fourth embodiment of the present invention will be described. This embodiment is also practiced on the basis of the procedures illustrated in FIGS. 3 and 5. The object to be diagnosed was a water-cooled turbine generator with a power of 1 GW that was during operation.

Instead of the gas collector shown in FIG. 4, a quadrupole mass spectrometer was directly attached to the turbine generator gas line. At this time, a fine flow valve capable of introducing a tiny amount of gas was attached between the gas line and the quadrupole mass spectrometer (step ST1).

A small amount of gas was constantly introduced from inside the turbine generator so that mass spectrometric data on organic substances could be obtained constantly on the spot (first data) (step ST2). The obtained data were transferred over a dedicated line so as to be continuously monitored at a separate monitor room.

As in the instant embodiment, data may be transmitted so that identification of organic substances and diagnosis may be performed in a place distant from the site of installation of the turbine generator. Alternatively, organic substances may be identified on the spot simultaneously with the withdrawal of the gas. If it is necessary to carry out the identification of organic substances and diagnosis frequently, online monitoring as done in the instant embodiment is advantageous in terms of work efficiency.

As a result of analysis, many relatively small molecular fragments with a mass number of 90 or less were detected, and relatively large molecular fragments with, say, mass numbers of 134 and 213 were also detected, in the first data from the mass spectrometry or organic substances present in the gas inside the turbine generator (step ST14). This analysis was unable to name the substances specifically, but the measurement of the mass numbers of molecular fragments alone often makes diagnosis possible.

Separately, a database was constructed beforehand (step ST3) which covered the molecular fragments of substances generated upon the decomposition by heat, discharge, corrosion or friction of three kinds of materials, including cured epoxy resins, the components inside the turbine generator (second data). This database was prepared by adding the existing database to the data we obtained.

Then, the molecular fragments (first data) detected in the turbine generator gas were checked against the database on the computer (step ST4). The molecular fragments with a mass number of 90 or less were detected not only in the turbine generator gas, but also in the gases generated from all of the three kinds of materials. Thus, these molecular fragments were difficult to use as an indicator for diagnosis of deteriorated materials.

Of the molecular fragments with a mass number of 90 or more, however, the molecular fragments with mass numbers of 134 and 213 detected in the gas inside the turbine generator were the only ones that agreed with molecular fragments of the gases generated, by heat, from the cured epoxy resins among the components inside the turbine generator. Thus, the fragments with mass numbers of 134 and 213 were utilized as standards of judgment for diagnosis of deteriorated materials (step S15).

The above agreement between the molecular fragments with mass numbers of 134 and 213 in the turbine generator gas and the molecular fragments of the gases generated, by heat, from the cured epoxy resins led to a diagnosis that the cured epoxy resins inside the turbine generator underwent heat deterioration (steps ST16, ST13).

In comparing the organic substances in the turbine generator gas with the gaseous substances evolved from constituent materials inside this apparatus, it may be difficult to compare all the substances that show consistency. In this case, a specific consistent substance or parameter which can be easily distinguishable from that of other component can be used as an indicator for diagnosis, as in the present embodiment.

To investigate the degree of deterioration by heat, changes over time in the intensities, i.e., concentrations, of the molecular fragments with mass numbers of 134 and 213 of organic substances in the gas inside the turbine generator were always monitored over the course of 1 month (step ST17). The intensities of the indicator molecular fragments were found to increase sharply at a rate of 10% in a week (step ST10).

Hence, a diagnosis was made that heat deterioration was rapidly proceeding in the cured epoxy resins inside the turbine generator, so that the turbine generator should be stopped and the materials renewed promptly (step ST11).

The instant embodiment adopted the method of directly installing an analyzer on the turbine generator to transfer data there and monitor it. The use of an analyzer other than the quadrupole mass spectrometer enables an online diagnosis to be made by exactly the same method.

Embodiment 5

The method for diagnosis as a fifth embodiment of the present invention will be described. This embodiment is practiced on the basis of the procedure illustrated in FIG. 5. The object to be diagnosed was a 400 MW turbine generator during trial operation shortly after renewal of the components inside the turbine generator.

In the same manner as in Embodiment 1, organic substances in the gas inside the turbine generator were trapped in an organic substance adsorption pipe 2 by the use of the device shown in FIG. 4 (step ST1). Then, the organic substances collected into the organic substance adsorption pipe were introduced via a heat desorbing device into a gas chromatograph with a mass spectrometer to analyze the organic substances in the turbine generator gas (step ST2).

Simultaneously with collection into the organic substance adsorption pipe 2, this pipe 2 was replaced by a glass tube. In the glass tube, two metal strips were placed to form a sample for analysis of substances adsorbed onto the surfaces of the metal strips. After the metal strips were taken out of the gas collector, their surfaces were analyzed by reflection infrared spectroscopy and X-ray photoelectron spectroscopy (step ST2).

The results of gas chromatography and mass spectrometry (first data) showed the presence of the aromatic hydrocarbons benzene and toluene, a plurality of aliphatic hydrocarbons, and a substance of an unknown structure with a molecular weight of about 126.

Analysis of the surfaces of the metal strips identified the above substance with a molecular weight of about 126 as melamine (step ST14).

The substance other than melamine identified by gas chromatography and mass spectrometry, namely, benzene, is an aromatic hydrocarbon with a molecular weight of less than 92, and thus was not utilized for diagnosis. Nor were the aliphatic hydrocarbons used for diagnosis.

Separately, organic substances generated from the components inside the turbine generator, i.e., cured epoxy resin, cured phenolic resin and cured melamine resin, by the action of heat or discharge were measured in advance (second data) to build a database (step ST3).

The aforementioned melamine, detected in the organic substances in the gas inside the turbine generator, was recognized in the second data, the measurements of the organic substances generated from the cured melamine resin by discharge (steps ST4, ST15).

Thus, it could be diagnosed that deterioration due to discharge occurred at the site in the turbine generator where the cured melamine resin was used (steps ST16, ST13). However, the portion where the cured melamine resin was used was judged not to pose a serious problem, if discharge took place there. Hence, this turbine generator was switched from trial operation to full-scale operation, without renewal of the components.

As in the instant embodiment, it is possible to diagnose a turbine generator during trial operation immediately after renewal of the components and judge whether to replace trial operation by full-scale operation.

The present invention provides a method for diagnosis of a deterioration or abnormality in components inside a turbine generator, but does not give a direct instruction on the operation of a main body of the turbine generator. Thus, even if any deterioration or abnormality is diagnosed as in the instant embodiment, operation may be continued unchanged, in view of the results of diagnosis.

While preferred embodiments of the present invention have been described, such descriptions are for illustrative purposes only, and it is to be understood that changes and modifications may be made therein without departing from the spirit and scope of the following claims.

What is claimed is:

1. A method for diagnosis of components inside a turbine generator, comprising:

collecting organic substances present in a gas inside a turbine generator;

measuring the organic substances collected to obtain first data for the organic substances;

measuring, before the collecting, organic substances generated from each component inside the turbine generator due to heat, discharge, corrosion, or friction, to compile second data for the organic substances; and comparing the first data to the second data to determine whether data in the second data is present in the first data.

2. The method for diagnosis of components inside a turbine generator as claimed in claim 1 comprising detecting changes over time in data in the first data that is also present in the second data.

3. The method for diagnosis of components inside a turbine generator as claimed in claim 1 comprising identifying a component undergoing deterioration, or determining the cause of deterioration of the component, on the basis of data in the first data that is also present in the second data.

4. The method for diagnosis of components inside a turbine generator as claimed in claim 1, including obtaining the first data and the second data by one of gas chromatography, infrared absorption spectroscopy, reflection infrared spectroscopy, mass spectrometry, and X-ray photoelectron spectroscopy.

5. The method for diagnosis of components inside a turbine generator as claimed in claim 1, including using a computer for the comparing of the first data to the second data.

6. The method for diagnosis of components inside a turbine generator as claimed in claim 1, wherein only data on aromatic hydrocarbons with a molecular weight of 92 or more among the first data and the second data are used as a standard for judgment in the comparing.

7. The method for diagnosis of components inside a turbine generator as claimed in claim 1, including passing the gas withdrawn from the turbine generator through an adsorbent to collect the organic substances in the gas inside the turbine generator.

* * * * *